United States Patent [19]

Lenker et al.

[11] Patent Number: 5,741,274
[45] Date of Patent: Apr. 21, 1998

[54] METHOD AND APPARATUS FOR LAPAROSCOPICALLY REINFORCING VASCULAR STENT-GRAFTS

[75] Inventors: Jay A. Lenker, Los Altos Hills, Calif.; Edward V. Kinney, Louisville, Ky.; Christopher K. Zarins; Thomas J. Fogarty, both of Portola Valley, Calif.

[73] Assignee: Cardio Vascular Concepts, Inc., Portola Valley, Calif.

[21] Appl. No.: 577,729

[22] Filed: Dec. 22, 1995

[51] Int. Cl.$^6$ ............................. A61B 17/02
[52] U.S. Cl. ............................. 606/142; 606/74
[58] Field of Search ............................. 606/139, 142, 606/74

[56] References Cited

U.S. PATENT DOCUMENTS

| | | | |
|---|---|---|---|
| 3,111,945 | 11/1963 | Von Solbrig | 606/74 |
| 3,657,744 | 4/1972 | Ersek | 3/1 |
| 4,140,126 | 2/1979 | Choudhury | 128/325 |
| 4,562,596 | 1/1986 | Kornberg | 623/1 |
| 4,577,631 | 3/1986 | Kreamer | 128/334 |
| 4,617,932 | 10/1986 | Kornberg | 128/334 |
| 4,787,899 | 11/1988 | Lazarus | 623/1 |
| 4,872,874 | 10/1989 | Taheri | 623/1 |
| 5,156,608 | 10/1992 | Troidl et al. | 606/142 |
| 5,174,276 | 12/1992 | Crockard | 128/4 |
| 5,309,896 | 5/1994 | Moll et al. | 128/20 |
| 5,361,752 | 11/1994 | Moll et al. | 128/20 |
| 5,368,600 | 11/1994 | Failla et al. | 606/142 |
| 5,372,147 | 12/1994 | Lathrop, Jr. et al. | 128/898 |
| 5,383,889 | 1/1995 | Warner et al. | 606/192 |
| 5,397,345 | 3/1995 | Lazarus | 623/1 |
| 5,522,823 | 6/1996 | Kuntz et al. | 606/142 |
| 5,527,355 | 6/1996 | Ahn | |
| 5,571,167 | 11/1996 | Maginot | |
| 5,584,879 | 12/1996 | Reimold et al. | |
| 5,593,414 | 1/1997 | Shipp et al. | 606/142 |

FOREIGN PATENT DOCUMENTS

| | | |
|---|---|---|
| 0539237A1 | 10/1992 | European Pat. Off. |
| 0573273A2 | 2/1993 | European Pat. Off. |
| 0579523A1 | 6/1993 | European Pat. Off. |
| 117981 | 1/1994 | European Pat. Off. |
| 0621016A1 | 4/1994 | European Pat. Off. |
| 2702951 | 9/1994 | France . |
| 1528459 | 8/1967 | U.S.S.R. . |
| WO9221291 | 12/1992 | WIPO . |
| WO9221293 | 12/1992 | WIPO . |
| WO9221294 | 12/1992 | WIPO . |
| WO9221295 | 12/1992 | WIPO . |
| WO9309722 | 5/1993 | WIPO . |
| WO9324063 | 12/1993 | WIPO . |
| WO9503754 | 2/1995 | WIPO . |
| WO9508289 | 3/1995 | WIPO . |
| WO9508952 | 4/1995 | WIPO . |

*Primary Examiner*—John G. Weiss
*Assistant Examiner*—John M. Black
*Attorney, Agent, or Firm*—Peninsula IP Group; Douglas A. Chaikin

[57] ABSTRACT

A method and apparatus for laparoscopically reinforcing blood vessels and vascular endoluminal prosthesis includes providing at least one reinforcing member. The endoluminal prosthesis having a sufficient hoop strength to inhibit collapse of the blood vessel. The reinforcing member constricts around the blood vessel to hold the endoluminal prosthesis with respect to the blood vessel and to inhibit aneurysmal growth.

2 Claims, 10 Drawing Sheets

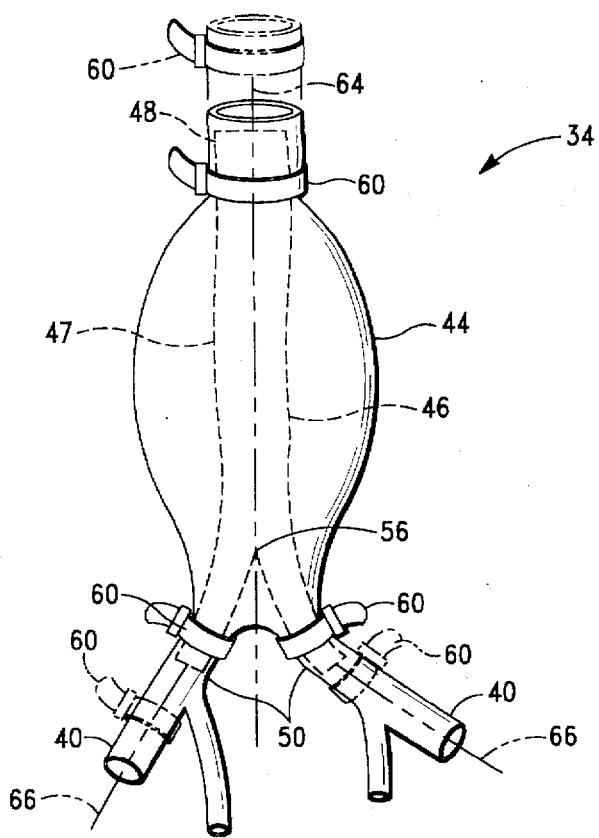
FIG.-5
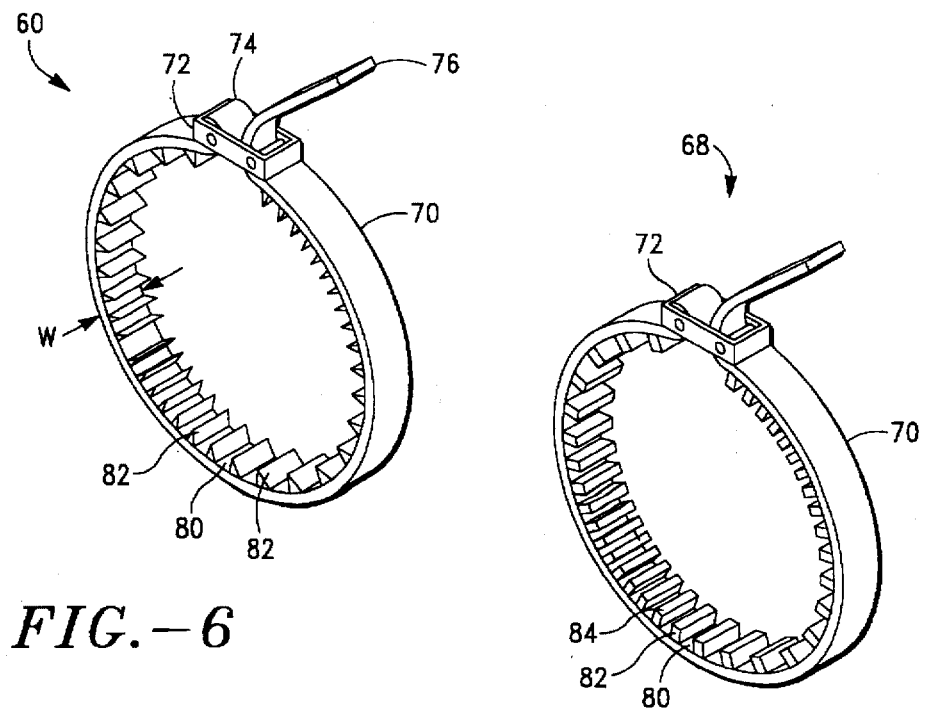
FIG.-6
FIG.-7

METHOD AND APPARATUS FOR LAPAROSCOPICALLY REINFORCING VASCULAR STENT-GRAFTS

BACKGROUND OF THE INVENTION

1. Field of the Invention

This invention relates generally to repairing vascular blood vessels. More particularly, this invention relates to reinforcing vascular stent-grafts.

2. Previous Art

An aneurysm is defined as a permanent abnormal dilation of a blood vessel wall which weakens the blood vessel. Often the diameter of the aneurysm is 50% greater than the normal blood vessel diameter. An aneurysm may grow larger. In severe cases, an aneurysm may rupture and cause severe internal bleeding. The risk of rupture increases with, among other things, the size and growth rate of the aneurysm.

Aneurysmal diseases including abdominal aortic aneurysms (AMs) are frequently diagnosed before a rupture occurs. AAAs are significant because the largest artery in the human body, namely the aorta, is affected. The diagnosed incidence of AAAs has increased over the last 20 years. AAAs typically appear in the aorta below the renal arteries, however approximately 5% of aortic aneurysms occur above the renal arteries. An AAA may, affect other regions of the aorta and also blood vessels such as the iliac, renal and visceral arteries.

The identification of AMs is often accomplished by radiographic evaluation. Abdominal films, for example, may demonstrate calcification of an aneurysmal wall. Abdominal ultrasound and magnetic resonance arteriohraphy examination are common diagnostic tools for identifying an AM. Once identified, the AAA may be treated by surgical techniques. It is often critical to treat an AAA before the AAA reaches advanced stages and before a rupture occurs since rupture is associated with a 90% mortality rate.

Aneurysmal disease is currently treated with open surgery. When an AAA is addressed with open surgery, the abdominal cavity is opened and the abdominal organs are displaced to enable access to the abdominal aorta which is located closely to the spine. The aorta is normally cross-clamped above and below the aneurysm and the diseased aortic segment is debrided of mural thrombus and atheroma through a longitudinal aortic incision. A synthetic vascular graft, typically made of woven polyester is sutured into healthy tissue at each end of the aneurysm. The aneurysmal aorta is wrapped around the prosthetic graft once homeostasis has been confirmed. The cross-clamps are then removed and the patient is closed. Such techniques are considered to be highly effective, however, open surgery and cross-clamping of the aorta may cause undesired complications. Open abdominal surgery requires extensive recovery time and is associated with several health risks. Cross-clamping the aorta during open surgery is associated with complications such as myocardial dysfunction, hemorrhage, infection, renal failure, impotency and gastrointestinal complications. What is desired is a way to treat AAAs without open surgery and especially without cross-clamping the aorta to minimize the risk of the development of complications.

Endovascular techniques are being developed to treat aneurysmal disease. A common endovascular technique includes placing an endoluminal prosthesis such as a graft within an aneurismic blood vessel. Such grafts may be stented or unstented and are typically fabricated from a synthetic material.

Grafts have been particularly effective when used within a diseased blood vessel such as an aneurysmal aorta. Grafts have also been used to bypass the aneurysm and safely direct blood around the aneurysmal blood vessel. Various endoluminal prosthesis other than grafts are being developed which insert within a blood vessel to repair diseased (e.g. stenotic) blood vessels.

Unstented grafts are often radially unsupportive although many of these unstented grafts are circumferentially crimped to improve hoop strength and kink resistance. Unstented grafts typically rely on blood pressure to maintain a desired shape. Some grafts are tubular in shape having a proximal and a distal end. Other grafts include bifurcated segments or branches which conform to the shape of a blood vessel. Many grafts are fabricated from a biologically compatible material such as Teflon® or woven polyester (e.g. Dacron®), for example. Unstented and otherwise unsupported endovascular grafts may not seal well or may become dislodged after a period of time. A better way of supporting an endovascular graft within a blood vessel is desired.

Stented grafts (stent-grafts), on the other hand, rely on a stent having a predetermined "hoop strength" to hold the graft in place and enable the stent-graft to radially support a blood vessel from within. Stent-grafts have an appropriate "hoop strength" to inhibit blood vessel collapse as well as stent-graft deformation. An example of a stent having an appropriate "hoop strength" is disclosed in U.S. Pat. No. 4,886,062 to Wiktor for an *"Intravascular Radially Expandable Stent and Method of Implant"*, the disclosure of which is incorporated herein by reference.

Known stent-grafts and grafting techniques have limitations. When an aneurysm having a stent graft grows, the stent-graft which seals off the aneurysm may dislodge as a result of the aneurysmal growth. In some cases, a gap may form between the graft and the blood vessel wall (see. FIG. 4), the blood may enter the gap and impose pressure between the graft and the blood vessel wall. This pressure could hasten aneurismic growth as well as dislodgment of the graft which may ultimately lead to aneurysmal rupture. A better way to inhibit aneurysmal growth is desired. A better way to secure endoluminal prosthesis such as stent-grafts without open surgery is also desired.

SUMMARY OF THE INVENTION

It is an object of this invention to provide a minimally invasive way to inhibit aneurysmal growth in the region of an endoluminal prosthesis such as a stent-graft.

It is another of object of this invention to provide a way of reinforcing various types of endoluminal prostheses such as an unstented graft, a stent-graft and other endoluminal prostheses within a blood vessel.

In accordance with the above objects, those mentioned and those which will become apparent below, the present invention includes a method useful in a body for laparoscopically reinforcing an endoluminal prostheses having a proximal end and a distal end, the steps of the method comprise:

- laparoscopically inserting a first reinforcing member into the body;
- manipulating a first reinforcing member to adjacent one end of the endoluminal prosthesis;
- reinforcing a substantial portion of the one end with the first reinforcing member;

securing the first reinforcing member with respect to the one end;

manipulating a second reinforcing member to adjacent another end of the endoluminal prosthesis;

reinforcing a substantial portion of the other end with the second reinforcing member; and securing the second reinforcing member with respect to the other end of the endoluminal prosthesis, whereby, when the reinforcing members insert laparoscopically into the body, the reinforcing members reinforce the endoluminal prosthesis.

In a preferred embodiment, the first and second reinforcing members surround each end of the endoluminal prosthesis to inhibit movement of the endoluminal prosthesis.

In another preferred embodiment, sutures secure each reinforcing member to the endoluminal prosthesis. The sutures inhibit movement of the endoluminal prosthesis. When the endoluminal prosthesis attaches to a region of the vasculature having an aneurysm, the sutures cooperate with the reinforcing members to inhibit aneurismal growth.

In another preferred embodiment, staples secure each reinforcing member to the endoluminal prosthesis. The staples inhibit movement of the endoluminal prosthesis. When the endoluminal prosthesis attaches to a region of the vasculature having an aneurysm, the staples cooperate with the reinforcing members to inhibit aneurismal growth.

In yet another embodiment, rivets secure each reinforcing member to the endoluminal prosthesis. The rivets inhibit movement of the endoluminal prosthesis. When the endoluminal prosthesis attaches to a region of the vasculature having an aneurysm, the rivets cooperate with the reinforcing members to inhibit aneurismal growth.

The present invention includes an apparatus for laparoscopically reinforcing an endoluminal prosthesis having a proximal end and a distal end, comprising:

a first reinforcing member capable of circumscribing the proximal end of the endoluminal prosthesis;

a second reinforcing member for capable of circumscribing the distal end of the endoluminal prosthesis;

a securing member attached to each reinforcing member for securing each reinforcing member with the endoluminal prosthesis;

whereby, the securing member secures the reinforcing member to reinforce the endoluminal prosthesis.

In a preferred embodiment, the reinforcing member includes a strap having a length and two ends. The straps conform in shape to circumscribe the endoluminal prosthesis. Each strap includes a corrugated surface for circumscribing vascularized blood vessels and inhibiting vascular necrosis.

In another preferred embodiment, the reinforcing member includes tapered teeth (which are in some circumstances blunted) for circumscribing vascularized blood vessels. Alternatively, radially moveable spikes impregnate the surface of the reinforcing member to hold the reinforcing member with the endoluminal prosthesis. The spikes move radially to hold the reinforcing member with a generally uniform force.

In another preferred embodiment, the securing member includes a strap having two ends. One end of the strap defines a loop. The other end of the strap feeds through the loop to lock the strap with the endoluminal prosthesis.

It is an advantage of this invention to a provide a minimally invasive way of reinforcing endoluminal prosthesis and to inhibit aneurysm growth.

BRIEF DESCRIPTION OF THE DRAWINGS

For a further understanding of the objects and advantages of the present invention, give reference to the following detailed description, taken in conjunction with the accompanying drawing, in which like parts have like reference numerals and wherein:

FIG. 5 is a perspective view of an embodiment of the present invention reinforcing the endoluminal prosthesis of FIG. 3.

FIG. 6 is a perspective view of the reinforcing member in accordance with the present invention.

FIG. 7 is a perspective view of the reinforcing member in accordance with the present invention.

DETAILED DESCRIPTION OF THE INVENTION

Figure 1:
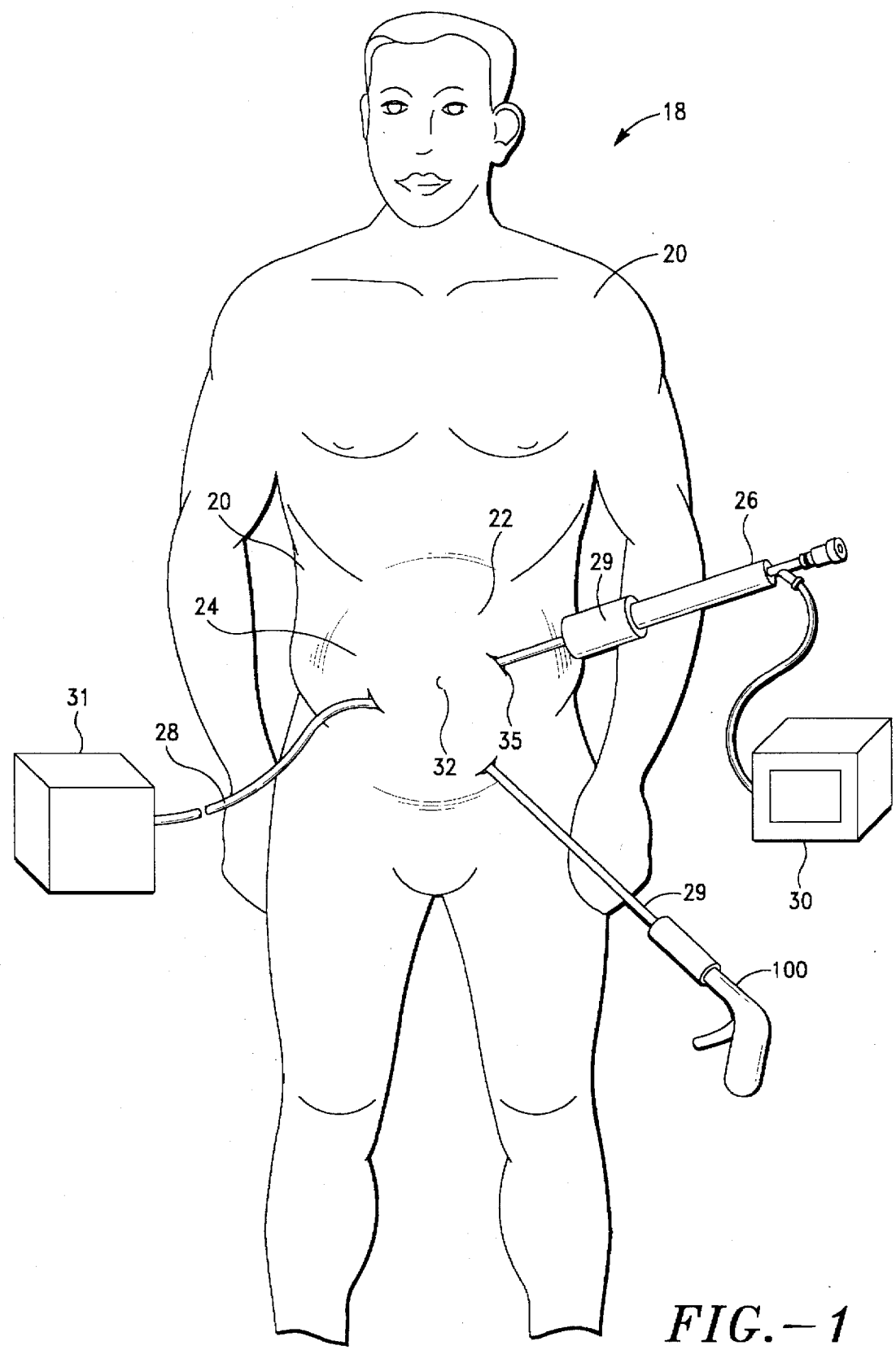
FIG. 1 is a perspective view of a laparoscopic procedure in accordance with the present invention.

With particular reference to FIG. 1, there is shown a body generally designated with the reference numeral 18 undergoing a laparoscopic procedure. The body 18 has an abdomen 20, a peritoneal cavity 22 and an abdominal wall 24 with an umbilicus 32. The method of the present invention employs a laparoscope 26, a gas insufflator 28, a trocar 29, and an imaging device 30, and a tool 100. The body 18 receives general anesthesia and is placed in a lithotomy position. A surgeon inserts the needle of the gas insufflator 28 below the umbilicus 32 and infuses gas into the peritoneal cavity 22. The gas, typically carbon dioxide, distends the abdomen 20 to enable visualization of the various abdominal organs within the peritoneal cavity 22. A regulator 31 continuously monitors and regulates the rate, pressure of the gas.

The surgeon inserts trocars 29 into the abdomen 20. The trocars 29 include a cannula and seals against the abdomen 20. Insertion of the trocar 29 makes an annular inframbilical puncture 35. Typically the infraumbilical puncture 35 is approximately 10 mm in diameter. The tool 100 inserts into the abdomen through one trocar 29.

The laparoscope 26 inserts into the peritoneal cavity 22 through one trocar 29. The laparoscope 26 includes an endoscope equipped with a light source and a magnifying lens. The light source illuminates selected regions within the peritoneal cavity 22 to reflect light and enable the magnifying lens to receive the reflected light. An imaging device 30 electronically attaches with the laparoscope 26 to receive images from the magnifying lens and to display the images to a laparoscope operator (e.g., the surgeon).

The surgeon looks through the laparoscope 26 to visualize the peritoneal cavity 22. Another small incision may be made in the abdominal wall 24 close to the infraumbilical puncture 35 to facilitate insertion of additional instruments into the peritoneal cavity 22. In certain instances, the additional instruments may be passed through the laparoscope or secondary trocar(s) (not shown). Such instruments may include surgical tools such as lasers, retractors, dissectors, (both the retractors and the dissectors may be coupled with balloons) cryosurgical and electrocautery devices. Such instruments may be used to dissect tissue to reach the aorta. Additionally, it is possible to measure the stump pressure of the inferior mesenteric artery with a laparoscopically placed probe. It will be appreciated that the inferior mesenteric artery may become ligated (tied or bound) and therefore cause problems in the bowel due to decreased blood flow to the area. At the end of the procedure, the surgeon removes the gas insufflator and the carbon dioxide gas, sutures the incisions and applies a dressing.

It will be appreciated that although the laparoscope 20 relies on light to image the peritoneal cavity, any of a variety of imaging devices may be employed in accordance with the present invention including those which do not rely on a light source. Additionally, the laparoscope 26 may be adapted for guiding any of a variety of diagnostic and surgical tools into the peritoneal cavity.

Advantages of employing laparoscopy in accordance with the present invention include time and cost efficiency. Experts associate relatively low morbidity rates and short convalescence periods with laparoscopic procedures when compared with open surgery.

Figure 2:
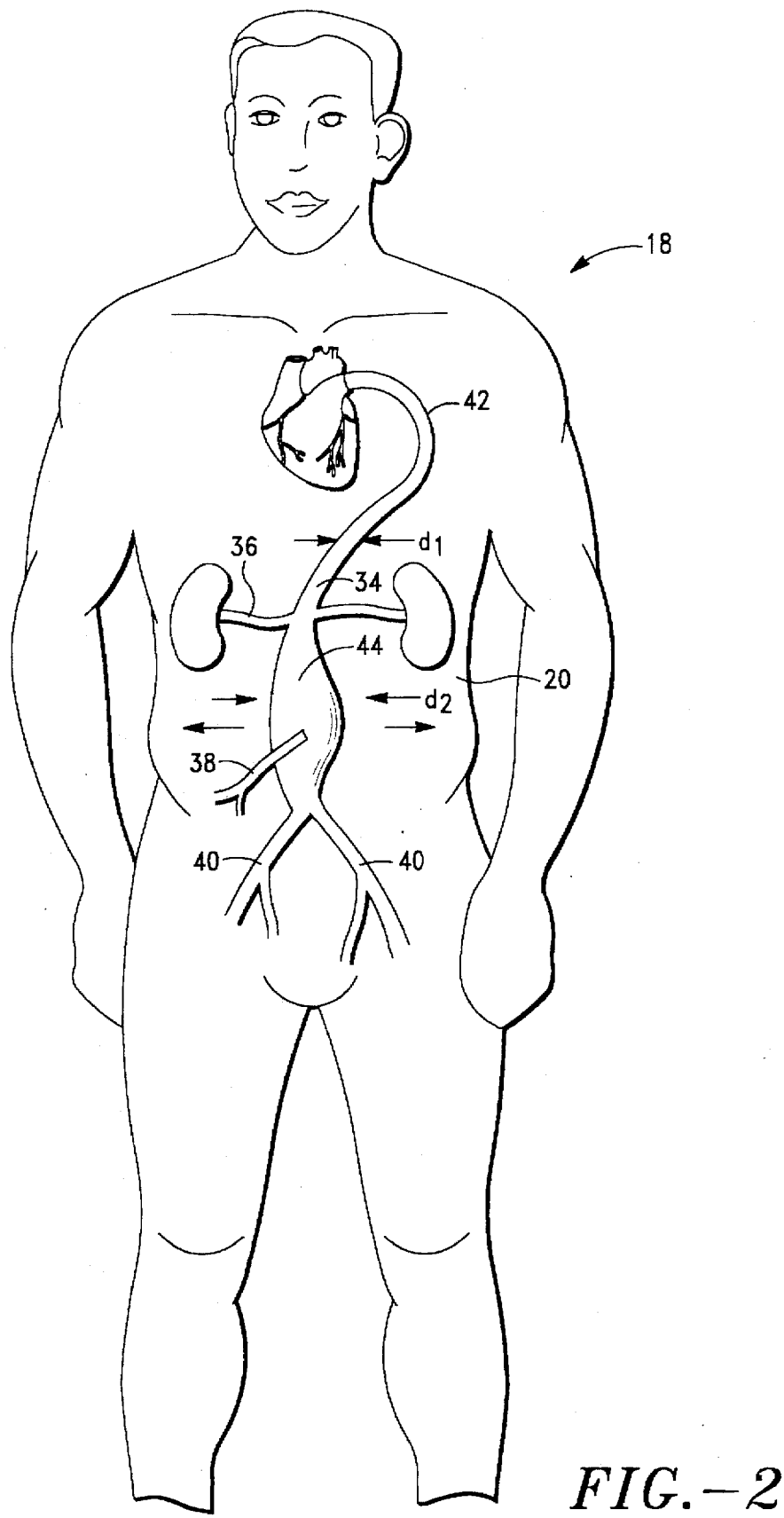
FIG. 2 is front view of an aneurismic blood vessel within a body.

With particular reference to FIG. 2, there is shown the body 18. The abdomen 20 has a blood vessel 42. The blood vessel 42 defines an aorta 34. The abdomen includes the renal 36, visceral 38 and iliac 40 blood vessels. The aorta 34 has an abdominal aortic aneurysm 44. A portion of the aorta 34 has a diameter designated as $d_1$. The AAA 44 has a diameter of $d_2$. The $d_2$ is at least 50% greater than the $d_1$. Current medical theory recommends surgery when the diameter of an aortic aneurysm is at least 50% greater than the normal diameter of the aorta.

Figure 3:
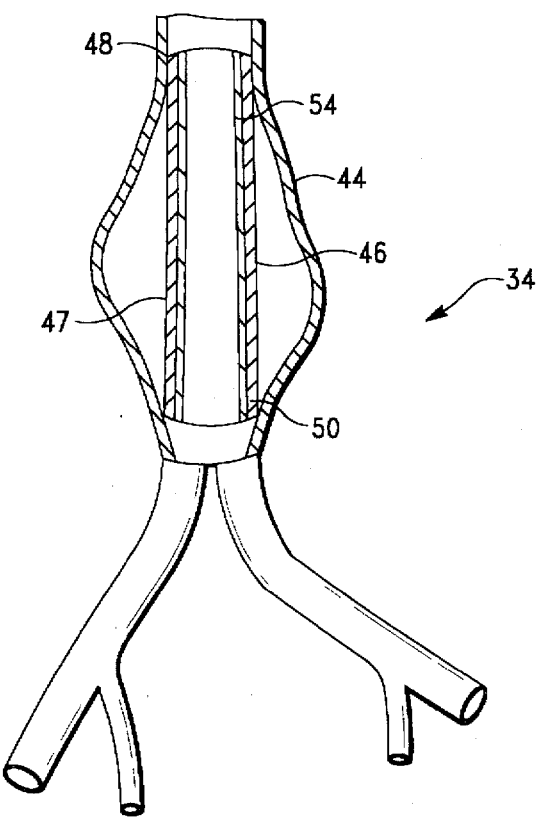
FIG. 3 is a cross-sectional view of the blood vessel of FIG. 2 with an endoluminal prosthesis.

With particular reference to FIG. 3, there is shown an aorta 34 having an AAA 44. An endoluminal prosthesis 46 attaches within the aorta 34 to bypass the AAA 44. The endoluminal prosthesis 46 includes a stent-graft 47. The stent-graft 47 includes a stent 54 and a fibrous graft made from Teflon® fiber. It can be appreciated that the endoluminal prosthesis 46 can include a graft, a stent or other items which enable normal functioning of the aorta 34.

The endoluminal prosthesis 46 has an anatomically proximal end 48 and an anatomically distal end 50. The endoluminal prosthesis 46 bypasses the aneurysm 44 to facilitate blood flow through the aorta 34, to reinforce the aorta 34 and to reduce the likelihood of aneurysm rupture. It is important to appreciate that the endoluminal prosthesis 46 is not limited to a stent-graft, and includes any prosthetic device for reinforcing a blood vessel wall.

It will be appreciated that numerous stents are on the market and each may be substituted for the stent 54 in accordance with the present invention. For example, an appropriate stent 54 is disclosed in U.S. Pat. No. 4,886,062 to Wiktor. The stent 54 may have a cage such as disclosed in U.S. Pat. Nos. 5,344,426, 5,443,500, 5,423,885 and 5,456,667. Additionally, the endoluminal prosthesis 46 may be deliverable and include a stent as disclosed in U.S. Pat. No. 5,458,615. The disclosures of these cited patents are incorporated herein by reference.

Although the endoluminal prosthesis 46 is shown within with the aorta 34, the endoluminal prosthesis 46 may be secured within a variety of blood vessels and other biological conduits by a variety of methods to facilitate operation of the present invention. For example, an endoluminal prosthesis 46 may be used with renal and reproductive conduits to repair injured areas or to bypass diseased areas.

Figure 4:
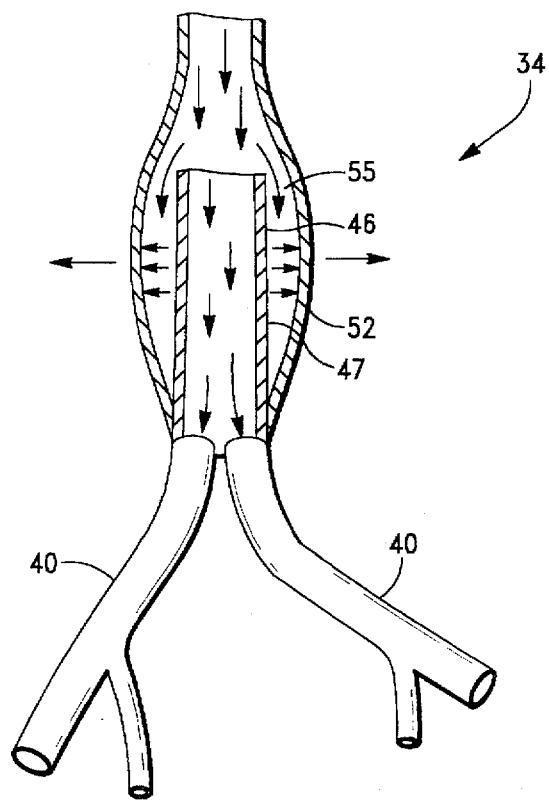
FIG. 4 is a cross-sectional view of the blood vessel of FIG. 3 having an enlarged and leaking abdominal aortic aneurysm AAA.

With particular reference to FIG. 4 there is shown the aorta 34 having an enlarged AAA 44. The aorta 34 has an aortic wall 52. Enlargement of the AAA 44 causes the aortic wall 52 to separate from the endoluminal prosthesis 46 and form a pocket 55. Separation of the endoluminal prosthesis 46 from the aorta 34 permits blood flow (indicated by the arrows) to enter the pocket 55 between the endoluminal prosthesis 46 and the aortic wall 52. This blood flow into the pocket 55 creates pressure which causes further separation of the endoluminal prosthesis 46 and the aortic wall 52. This condition is not only highly undesirable but dangerous. Leaks around or dislodgment of the endoluminal prosthesis 46 may result in rupture of the AAA 44 which is normally fatal.

With particular reference to FIG. 5, there is generally shown the aorta 34. the aorta 34 has an AAA 44. The vascular endoluminal prosthesis 46 includes a stent-graft 47 that attaches within the aorta 34 and bypasses the AAA 44. The endoluminal prosthesis 46 is bifurcated having a fork 56. The endoluminal prosthesis 56 has two anatomically distal ends 50 that extend to within the iliac arteries 40. The proximal end 48 of the endoluminal prosthesis 46 and the distal ends 50 attach within the aorta 34 and the two iliac arteries 40, respectively.

In one embodiment of the present invention a reinforcing member 60 circumscribes each distal end 50 and the proximal end 48 to reinforce the endoluminal prosthesis 56. The reinforcing member 60 is preferrably placed external to the arery or vessel. The reinforcing member 60 prevents the seal between the endovascular prosthesis and vessel wall from being compromised.

In another embodiment of the present invention (shown in phantom), the reinforcing member 60 is positioned proximal each distal end 50 and proximal end 48 to reinforce the endoluminal prosthesis 46. As shown in phantom, the reinforcing member 60 reinforces each end of the endoluminal prosthesis 46 by constricting about a portion of the aorta 34 adjacent each end of the endoluminal prosthesis 46.

Figure 18:
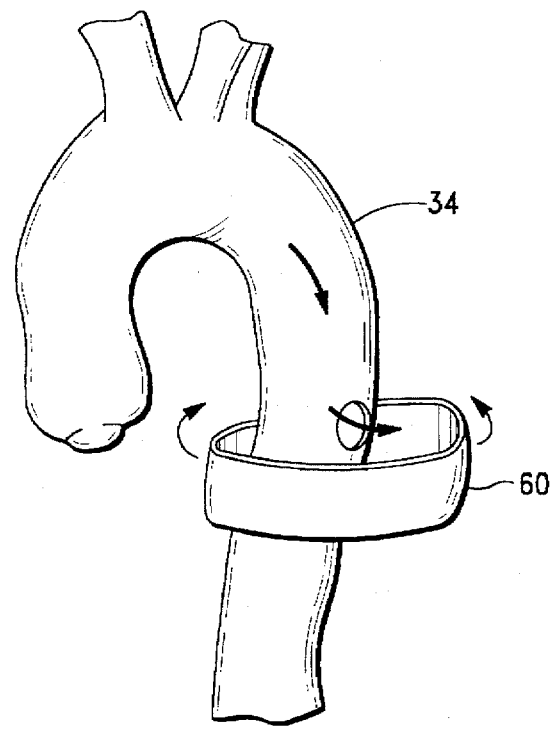
FIG. 18 illustrates the embodiment of the invention wherein one and only one reinforcing member is used.

In yet another embodiment, shown in FIG. 18, there is one and only one reinforcing member 60. In this embodiment, the reinforcing member 35 is placed around the aneurysm where there is no distal cuff, which makes stenting in this area difficult. The reinforcing member 60 is placed around the area adjacent the arota as shown in FIG. 18.

It will be appreciated that various endoluminal prostheses are anticipated by the present invention including those which feed into the aorta 34 as a fluid and harden to fill a portion of the aneurysm 44. Additionally, an endoluminal prosthesis may be a graft, a stent or a stent-graft 47 for examples.

The aorta 34 has an axis 64 and each iliac artery has an axis 66. The reinforcing members 60 surround each end of the endoluminal prosthesis 34 to inhibit separation of the endoluminal prosthesis 46 from the aortic wall 52. The reinforcing members 60 also inhibit aneurismal growth along the respective axis' 64 and 66. The reinforcing members 60 hold the endoluminal prosthesis 46 with the aorta 34 to inhibit separation of the endoluminal prosthesis 46 from the aorta 34 when aneurysmal growth occurs such as shown in FIG. 4. The reinforcing members 60 reinforce the aorta 34 and the endoluminal prosthesis 46 to inhibit radial deformation of each. The reinforcing members 60 inhibit lateral movement such as slippage between the aorta 34 and the vascular endoluminal prosthesis 46.

It will be appreciated that although the reinforcing members 60 are shown with an aorta 34, the reinforcing members are also capable of use in various biological conduits including other blood vessels and any of a variety of other biological conduits having endoluminal prosthesis. Although the reinforcing members 60 surround the aorta 34, the reinforcing members 60 may surround a portion of the aorta 34 to effectively reinforce an endoluminal prosthesis such as the stent graft 47.

The endoluminal prosthesis 46 has a hoop strength sufficient to resist deformation such as radially inward deformation. Aneurysmal growth or inward thrombus proliferation, for example, may cause such deformation of the endoluminal prosthesis 34. The endoluminal prosthesis 34 has sufficient hoop strength to support the reinforcing members 60 when the reinforcing members 60 squeeze the aorta 34 against the endoluminal prosthesis 46.

With particular reference to FIG. 6, there is shown one embodiment of the reinforcing member 60. The reinforcing member 60 is fabricated from a biologically compatible material such as a material chosen from the group consisting essentially of polyester, polypropylene, polyethylene, and Teflon®.

The reinforcing member 60 includes a strap 70 and securing member 72. The strap 70 has two ends 74 and 76. The securing member 72 adjustably locks the end 74 to a selected section of the strap 70. In another embodiment, the securing member 72 locks both ends 72 and 76 of the strap 70 together.

The reinforcing member 60 is flexible and has a width "w" of less than 15 mm to enable laparoscopic delivery through a trocar sheath having a diameter within the range of 10–15 mm.

The reinforcing member 60 includes a textured surface 80. Arteries including the aorta 34 are vascularized (contain blood vessels). The textured surface 80 regulates the distribution of force between the reinforcing member and the endoluminal prosthesis to facilitate blood flow through the aorta that is a vascularized blood vessel. Regulation of the distribution of force minimizes the risk of artery wall necrosis. The surface 80 of the reinforcing member includes multiple teeth 82 that grip endoluminal prostheses.

With particular reference to FIG. 7 there is shown an embodiment of the reinforcing member generally designated with the reference numeral 68. The textured surface 80 is corrugated. The teeth 82 have blunt ends.

When the textured surface 80 constricts around a blood vessel such as the aorta having an aneurysm, the textured surface grips the blood vessel and non-uniformly applies pressure to the blood vessel. The teeth 82 align closely having a spacing that restricts aneurismal growth.

It will be appreciated that the pressure applied by the textured surface 80 against a blood vessel may vary in direction and magnitude according to the texture of the surface 80. Accordingly, the texture is adaptable to optimize restriction of aneurismal growth and to maximize reinforcement of endoluminal prosthesis. Reinforcement of endoluminal prosthesis includes securing the endoluminal prosthesis with respect to the blood vessel.

Figure 8:
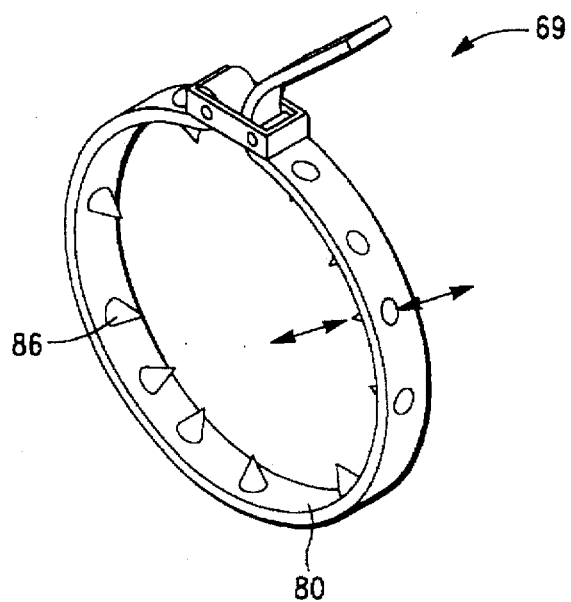
FIG. 8 is a perspective view of the reinforcing member in accordance with the present invention.

With particular reference to FIG. 8, there is shown an embodiment of the reinforcing member generally designated with the reference numeral 69. The textured surface 80 includes pointed spikes 86 for holding the reinforcing member 69 with a blood vessel. When the reinforcing member attaches to a blood vessel having an endoluminal prosthesis in the region of an aneurysm, the spikes 86 move to distribute compressive forces from the spikes 86 to an endoluminal prosthesis. The spikes 86 hold the endoluminal prosthesis while inhibiting blood vessel necrosis. The spikes 86 hold the reinforcing member 69 so that the reinforcing member 69 need not constrict the blood vessel to be held.

The spikes 86 are normally biased to extend radially inward from the textured surface 80. The spikes 86 slide radially outward from the reinforcing member 60 when compressive forces between the reinforcing member and the endoluminal prosthesis exceed a predetermined value, for example. This may occur when a spike 86 urges against a calcific portion of a blood vessel wall, for example. Radial movement of the spikes 86 enables the reinforcing member 60 to maintain a desired radius of curvature around a blood vessel to inhibit aneurismal growth.

Figure 9:
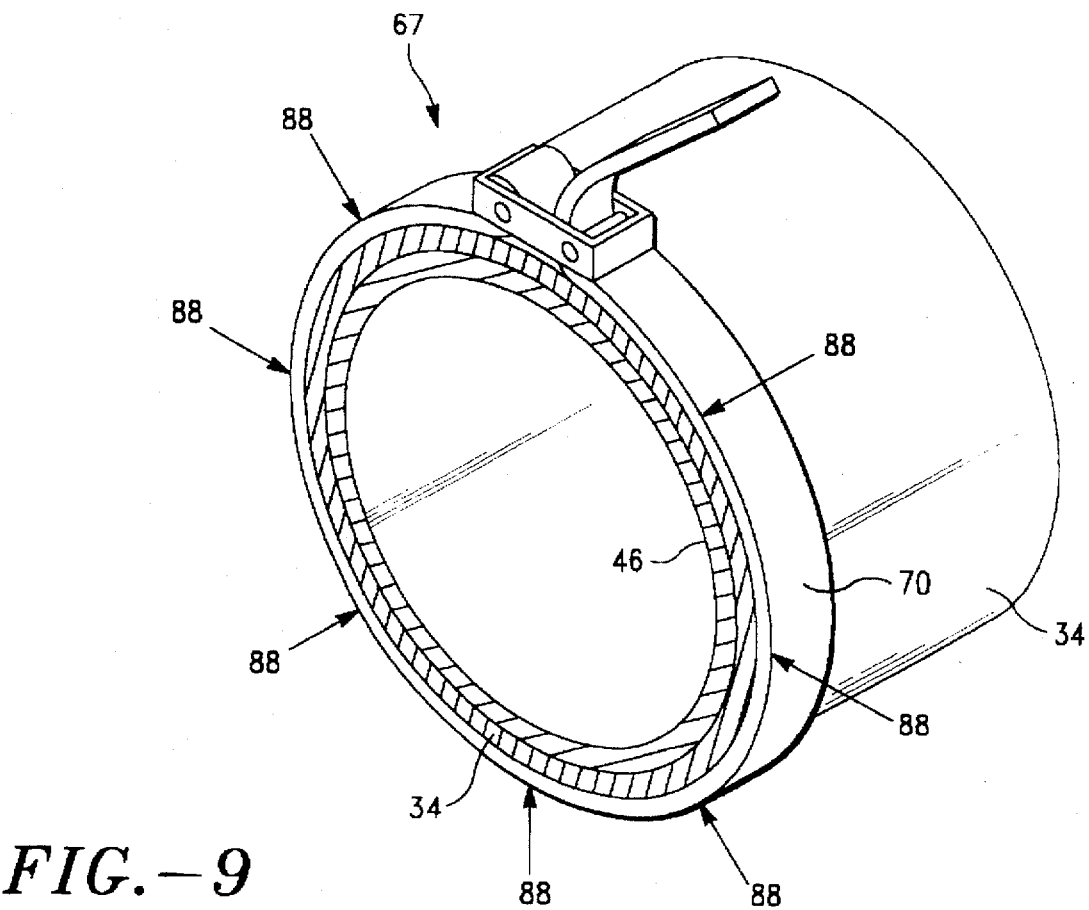
FIG. 9 is a cross-sectional view of an endoluminal prosthesis and a reinforcing member in accordance with the present invention.

With particular reference to FIG. 9 there is shown the reinforcing member generally designated with the reference numeral 67. The reinforcing member 67 attaches with the aorta 34 and the endoluminal prosthesis 46. The reinforcing member 67 circumscribes the aorta 34 and the endoluminal prosthesis 46. The strap 70 adjustably constricts about the aorta 34 to enable the reinforcing member 67 to adjustably impose a compressive force against the endoluminal prosthesis 46 in the direction indicated by radially inward arrows 88. The endoluminal prosthesis 46 urges radially outward against the reinforcing member 60 with a force that opposes the compressive force imposed by the reinforcing member 60 to hold the endoluminal prosthesis 46 with respect to the aorta 34. The reinforcing member 67 enables the endoluminal prosthesis 46 to maintain a predetermined shape. The reinforcing member 67 cooperates with the endoluminal prosthesis 46 to inhibit expansion of the aorta 34, to inhibit aneurysmal growth, to inhibit movement of the endoluminal prosthesis and to maintain a seal between the endoluminal prosthesis 46 and the aorta 34. Cooperation between the reinforcing member 67 and the endoluminal prosthesis 46 inhibits aortic collapse and necrosis of the aorta 34 and maintains prothesis in apposition with the vessel wall.

Figure 10:
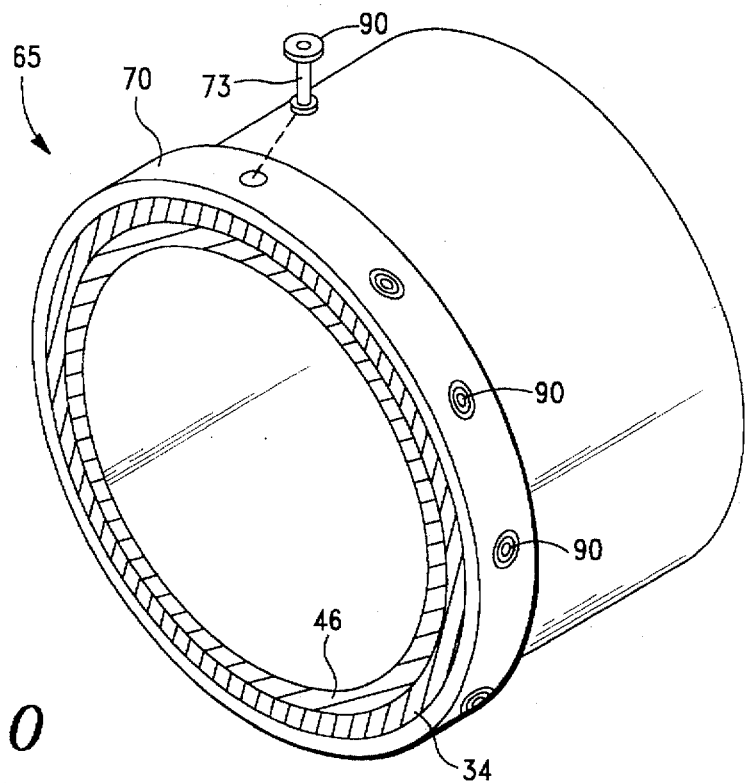
FIG. 10 is the reinforcing member in accordance with the present invention riveted to an endoluminal prosthesis.

With particular reference to FIG. 10 there is shown the reinforcing member 65 and the securing member 73. The strap 70 includes a continuous ring. The securing member 73 includes rivets 90. The rivets 90 secure the reinforcing member 65 to the endoluminal prosthesis 46 and cooperate with the reinforcing member 65 to inhibit aneurysmal growth. The rivets 90 are uniform in length to maintain the reinforcing member 65 at a desired distance from the endoluminal prosthesis 46 to inhibit blood vessel necrosis.

Figure 11:
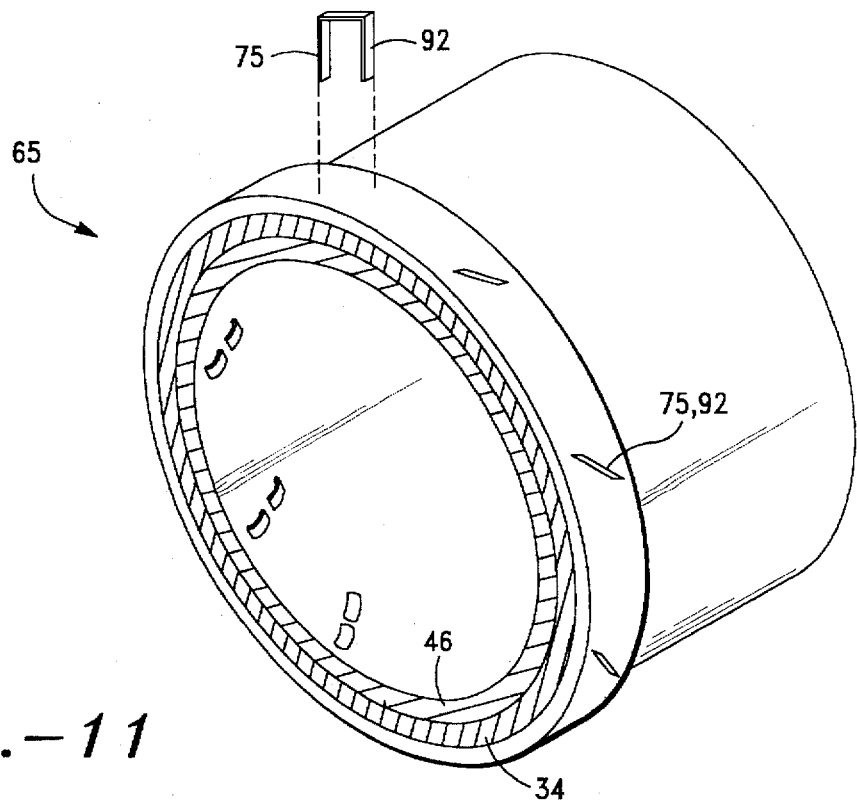
FIG. 11 is the reinforcing member in accordance with the present invention stapled to an endoluminal prosthesis.

With particular reference to FIG. 11, there is shown the reinforcing member 65 and the securing member 75. The securing member 75 includes staples 92. The staples 92 have a wire diameter designed for puncturing live tissue without causing significant injury (e.g. necrosis) to live tissue such as a blood vessel wall. Accordingly, the when staples 92 attach the reinforcing member 65 to the endoluminal prosthesis, the staples 92 cooperate with the reinforcing member 65 to inhibit aneurismic growth.

Figure 12:
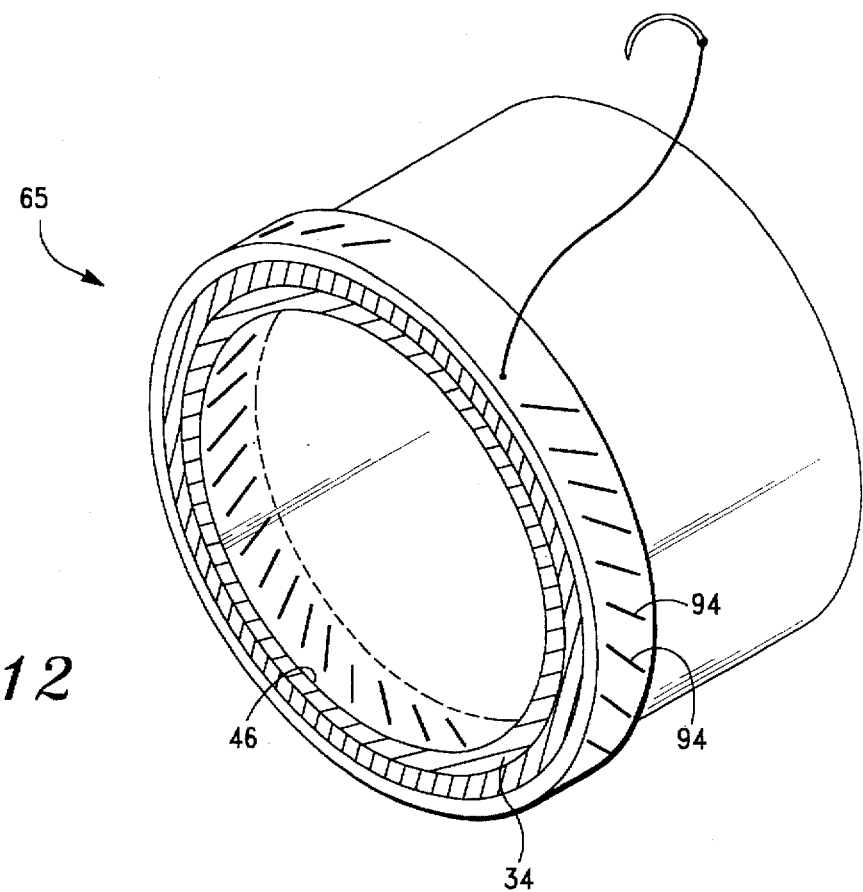
FIG. 12 is the reinforcing member in accordance with the present invention sutured to an endoluminal prosthesis.

With particular reference to FIG. 12, there is shown the reinforcing member 65 and sutures 94. The sutures 94 firmly secure the reinforcing member 79 with the endoluminal prosthesis 46 to inhibit movement of the endoluminal prosthesis 46. When the endoluminal prosthesis 46 attaches to a blood vessel having an aneurysm, the sutures 94 attach the blood vessel wall to the endoluminal prosthesis to inhibit aneurismal growth.

It will be appreciated that each securing member embodiment disclosed herein attaches the reinforcing member 65 along a desired radius of curvature about a blood vessel. Each securing member disclosed secures the endoluminal prosthesis 46 with a generally uniform force that avoids injury to the blood vessel and restricts aneurismic growth.

Figure 13:
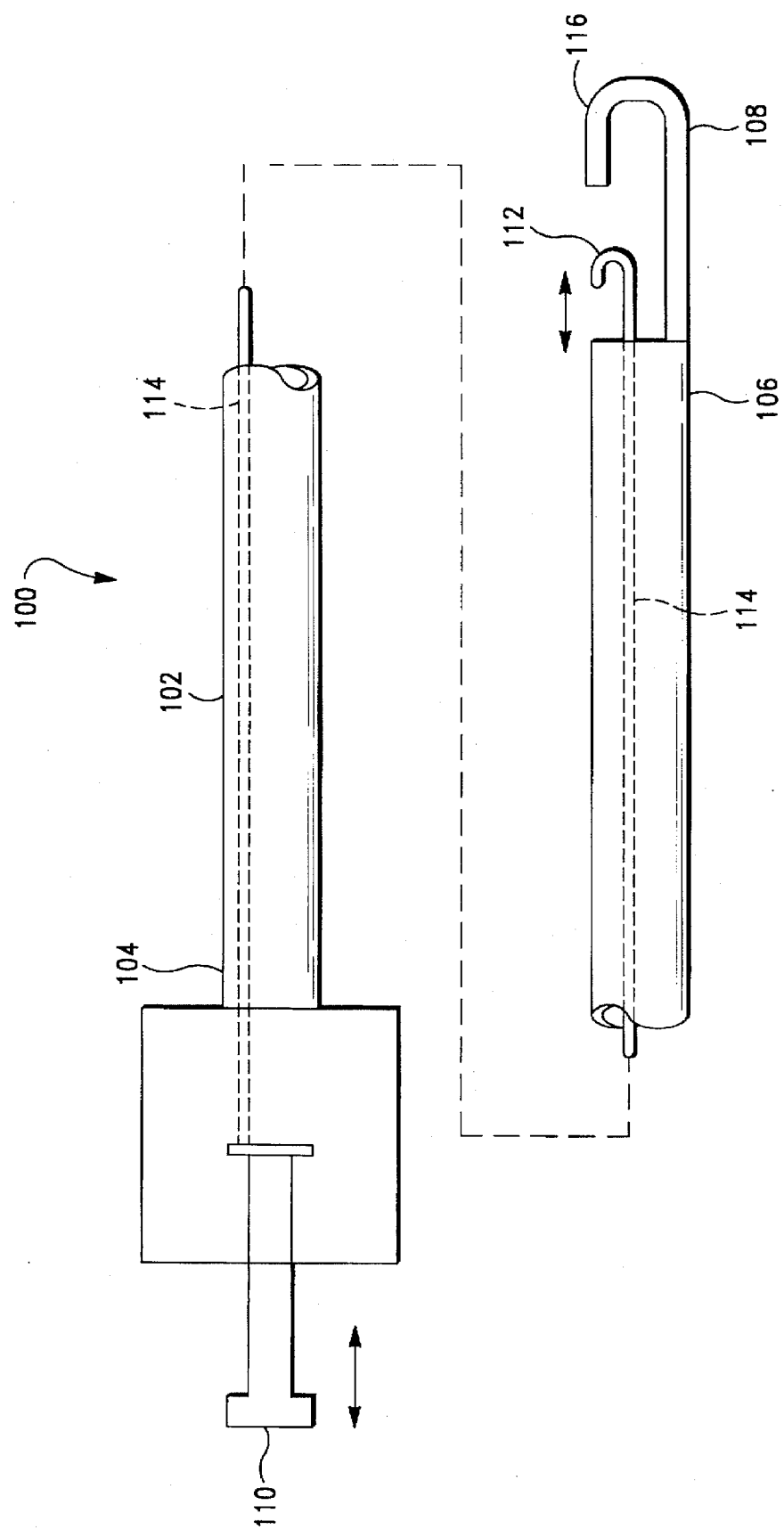
FIG. 13 is a tool for laparoscopically positioning the reinforcing member in a body in accordance with the present invention.

With particular reference to FIG. 13, there is shown a tool generally designated with the reference numeral 100. The tool 100 includes a catheter body 102 with a proximal end 104 and a distal end 106, a guide 108, an actuator 110, and a hook 112. The proximal end 104 of the tool 100 is laparoscopically insertable into a body via the laparoscope 26 (FIG. 1) or another trocar (not shown).

The guide 108 is formed having an arcuate arm 116 that extends from the distal end 106 of the catheter body 102 for holding a reinforcing member. The guide 108 attaches to the distal end 106 for guiding the reinforcing member about a blood vessel.

The actuator 110 attaches with the proximal end 104 of the catheter body 102. A cable 114 interconnects the actuator 110 with the hook 112. The hook 112 slidably movably mounts on the distal end 106 of the catheter body 102. The hook 112 locks the reinforcing member 67 about the endoluminal prosthesis 46 (FIG. 9) in response to movement of the actuator 110.

Figure 14:
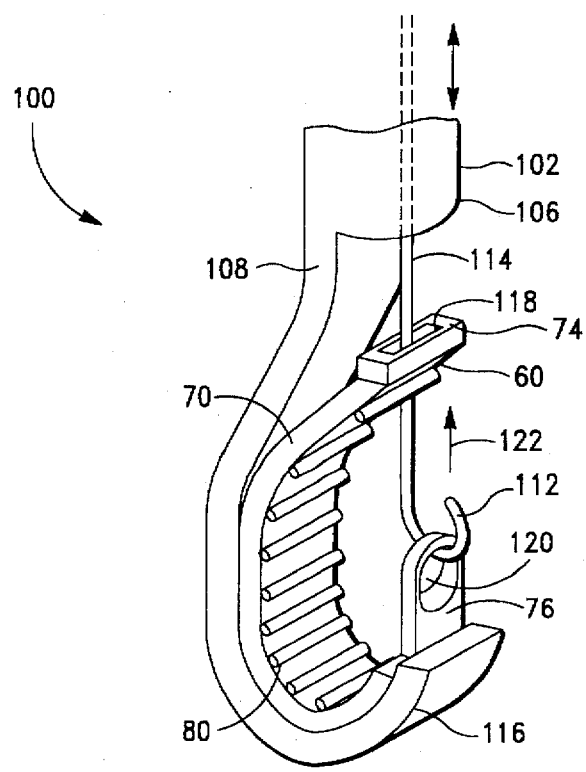
FIG. 14 is an embodiment of the distal end of the tool of FIG. 13.

With particular reference to FIG. 14, there is shown the tool 100 having the guide 108 attached to the distal end 106 of the catheter body 102. The guide 108 holds the strap 70 of the reinforcing member 60. The end 74 of the strap 70 defines a slot 118 for receiving the end 76 of the strap 70. The end 76 defines an opening for receiving the hook 112.

The hook 112 is formed integral with the cable 114. The cable 114 inserts through the slot 118 and the hook 112 inserts within the opening 120. In response to movement of the cable 114 in the direction of the arrow 122, the hook 112 draws the end 76 of the strap 70 through the other end 74 of the strap 70. The slot 118 locks with the textured surface 80 of the strap 70. When the cable 114 draws the hook 112 in the direction of the arrow 122, the arcuate arm 116 of the guide 108 directs the end 76 of the reinforcing member 60 through the slot 118.

Figure 15:
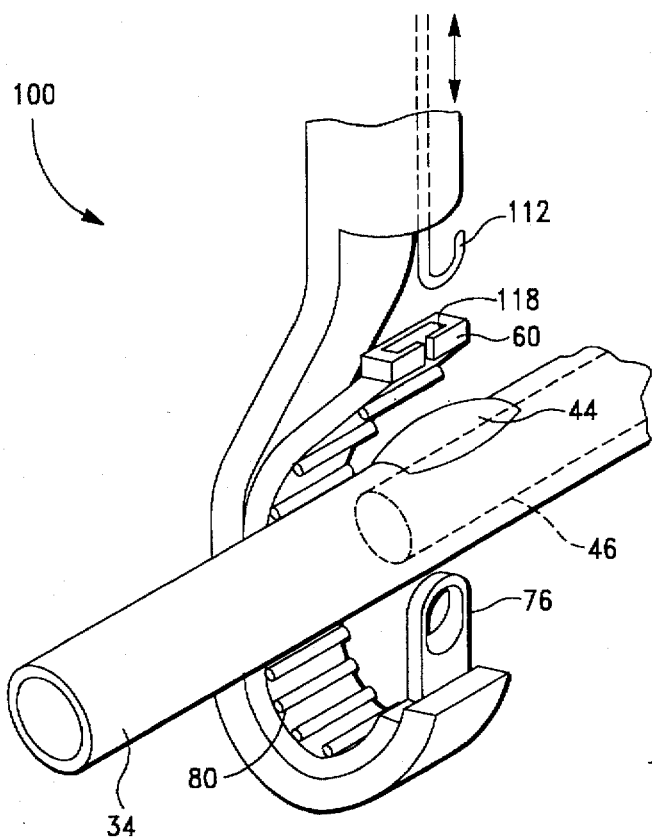
FIG. 15 is the distal end of the tool of FIG. 13 adjacent an aneurismic blood vessel.

With particular reference to FIG. 15, there is shown the tool 100 holding the reinforcing member 60 adjacent the aorta 34. The hook 112 inserts through the slot 118 of the reinforcing member 60. The hook 112 grasps the end 76 of the reinforcing member 60 and attaches the reinforcing member 60 about the aorta 34.

Figure 16:
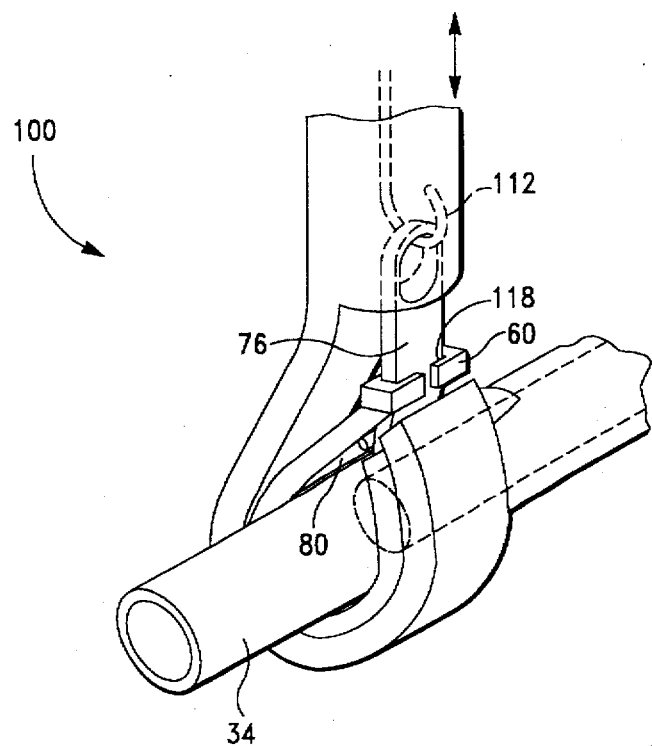
FIG. 16 is the distal end of the tool of FIG. 13 attaching the reinforcing member to the aneurysmal blood vessel of FIG. 15.

With particular reference to FIG. 16, there is shown the tool 100 which pulls the reinforcing member around the aorta 34. The tool 100 adjustably attaches the reinforcing member 64 around the aorta 34. Each reinforcing member 60 adjustably compresses the endoluminal prosthesis 46 and a portion of the aorta 34 together to secures the endoluminal prosthesis 46 within the aorta 34.

Figure 17:
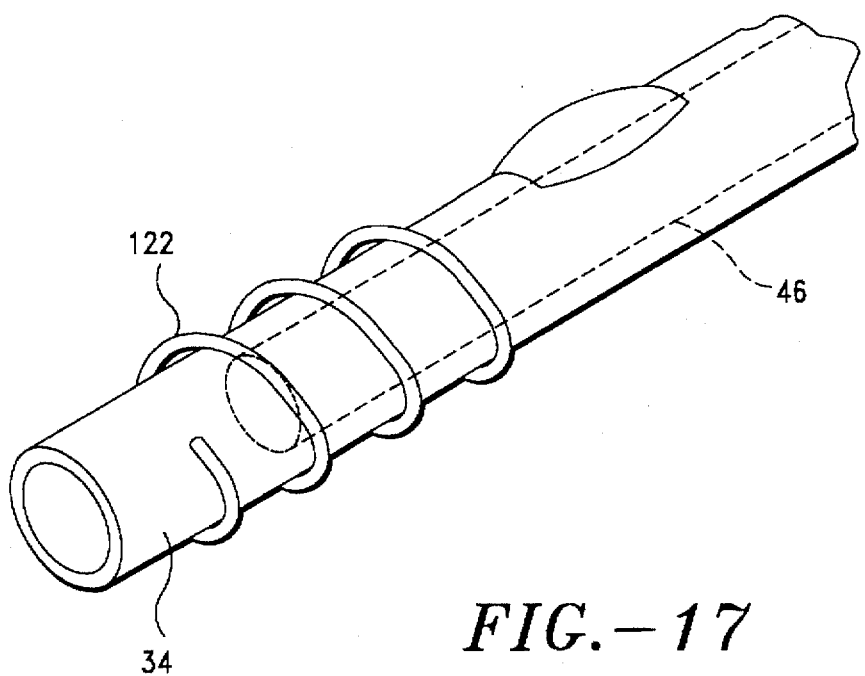
FIG. 17 is an embodiment of the reinforcing member in accordance with the present invention.

The hook 112 hooks the end 76 of the reinforcing member 60 and draws the end 76 through the slot 118 as chosen particularly in FIG. 17. The slot 118 locks against the textured surface 80 of the reinforcing member.

The tool 100 compresses the reinforcing member 60 about the endoluminal prosthesis 46 with a radial force exceeding the normal hoop strength of a healthy aorta. The endoluminal prosthesis 46 includes a hoop strength that is at least equivalent to the radial force exerted by the reinforcing member 60 to inhibit collapse of the aorta.

As shown, the reinforcing member 60 circumscribes the endoluminal prosthesis 46. Appreciate that the reinforcing member 60 may partially surround the endoluminal prosthesis 46.

With particular reference to FIG. 17, there is shown the reinforcing member 122 surrounding the endoluminal prosthesis 46 in a helical pattern. The reinforcing member 122 being a pretensioned metal to retain a helical shape and to hold the endoluminal prosthesis 46 with the aorta 34.

While the foregoing detailed description has described several embodiments of the method and apparatus for laparoscopically reinforcing an endoluminal prosthesis in accordance with this invention, understand that the above description is illustrative only and not limiting of the disclosed invention. Particularly, the reinforcing member 60 need not surround the endoluminal prosthesis 46. Instead, the reinforcing member 60 can constrict a blood vessel adjacent each end of the endoluminal prosthesis 46 to inhibit movement of the endoluminal prosthesis 46 and to inhibit aneurysmal growth. Additionally, the reinforcing member 60 may assume a variety of shapes and need not include securing member, but may be rigid or spring loaded to conform to a predetermined shape. Additionally, while use of the present invention with the aorta is shown, the present invention can be used with any of a variety of blood vessels and other biological conduits having an endoluminal prosthesis. It will be appreciated that the embodiments discussed above and the virtually infinite embodiments that are not mentioned could easily be within the scope and spirit of this invention. Thus, the invention is to be limited only by the claims as set forth below.

What is claimed is:

1. A tool used in conjunction with a reinforcing member for laparoscopically reinforcing a vascular endoluminal prosthesis, comprising:

a catheter insertable through a trocar, for laparoscopically inserting a reinforcing member to adjacent an aneurismic blood vessel, the catheter having a proximal end and a distal end;

a guide attached to the distal end for guiding the reinforcing member about a blood vessel, the guide has an arcuate arm which extends from the distal end of the catheter and holds the reinforcing member, the reinforcing member has a first end which defines a loop, and a second end, the guide holds the reinforcing member, the moveable means includes a hook which extends through the loop to pull the second end of the reinforcing member through the loop to lock the reinforcing member;

an actuator attached to the proximal end of the catheter; and a moveable means attached to the actuator, the moveable means being movably mounted on the distal end of the catheter to lock the reinforcing member about the endoluminal prosthesis in response to the actuator, whereby, when the catheter laparoscopically inserts a reinforcing member through the trocar into a body to adjacent an aneurismic blood vessel, the actuator locks the reinforcing member to reinforce the endoluminal prosthesis.

2. A tool used in conjunction with a reinforcing member for laparoscopically reinforcing a vascular endoluminal prosthesis, comprising:

a catheter insertable through a trocar, for laparoscopically inserting a reinforcing member to adjacent an aneurismic blood vessel, the catheter having a proximal end and a distal end;

a guide attached to the distal end for guiding the reinforcing member about a blood vessel;

an actuator attached to the proximal end of the catheter; and a moveable means attached to the actuator, the moveable means being movably mounted on the distal end of the catheter to lock the reinforcing member about the endoluminal prosthesis in response to the actuator, the moveable means includes a hook, the arcuate arm of the guide directs the second end of the reinforcing member through the loop when the hook pulls the second end, whereby, when the catheter laparoscopically inserts a reinforcing member through the trocar into a body to adjacent an aneurismic blood vessel, the actuator locks the reinforcing member to reinforce the endoluminal prosthesis.

* * * * *